US00PP25877P3

(12) United States Plant Patent
Klemm et al.

(10) Patent No.: US PP25,877 P3
(45) Date of Patent: Sep. 8, 2015

(54) ***DIANTHUS* PLANT NAMED 'KLEDG13146'**

(50) Latin Name: ***Dianthus* sp.**
Varietal Denomination: KLEDG13146

(71) Applicant: Klemm+Sohn GmbH & Co. KG, Stuttgart (DE)

(72) Inventors: Nils Klemm, Stuttgart (DE); Martin Glawe, Stuttgart (DE)

(73) Assignee: Klemm+Sohn GmbH & Co. KG, Stuttgart (DE)

( * ) Notice: Subject to any disclaimer, the term of this patent is extended or adjusted under 35 U.S.C. 154(b) by 149 days.

(21) Appl. No.: 13/998,180

(22) Filed: Oct. 9, 2013

(65) Prior Publication Data

US 2015/0101092 P1 Apr. 9, 2015

(51) Int. Cl.
*A01H 5/02* (2006.01)

(52) U.S. Cl.
USPC ..... Plt./273

(58) Field of Classification Search
USPC ..... Plt./272, 273
See application file for complete search history.

(56) References Cited

U.S. PATENT DOCUMENTS

PP9,758 P * 12/1996 Sapia ..... Plt./278

* cited by examiner

*Primary Examiner* — Anne Grunberg
(74) *Attorney, Agent, or Firm* — James M. Weatherly; Barbara Campbell; Cochran Freund & Young LLC

(57) ABSTRACT

A new *Dianthus* plant particularly distinguished by having single flowers with a blue-violet flower color; rich flowering; and medium growth, is disclosed.

1 Drawing Sheet

Genus and species: *Dianthus* sp.
Variety denomination: 'KLEDG13146'.

BACKGROUND OF THE NEW PLANT

The present invention comprises a new and distinct variety of garden carnation, botanically known as *Dianthus* sp. and hereinafter referred to by the variety name 'KLEDG13146'. 'KLEDG13146' originated from a controlled-cross between the proprietary female *Dianthus* variety 'DCP 06 060' (unpatented) and the male *Dianthus Gratianopolitanu* variety 'N6' (unpatented).

In May 2007, two *Dianthus* parental lines, 'DCP 06 060' and 'N6' were crossed via a controlled-cross in Stuttgart, Germany and seeds were obtained. The seeds were sown and plants were grown for evaluation. A plant line was selected in June 2008, and subsequently named 'KLEDG13146'. In June 2008, 'KLEDG13146' was first vegetatively propagated by vegetative cuttings in Stuttgart, Germany. 'KLEDG13146' was found to reproduce true to type in successive generations of asexual propagation via vegetative cuttings.

CROSS REFERENCE TO RELATED APPLICATIONS

Plant Breeder's Rights for 'KLEDG13146' were applied for in Canada on Feb. 8, 2013, Application No. 13-7917 and in Switzerland on Jun. 6, 2013 as Application No. 13-2861. 'KLEDG13146' has not been made publicly available or sold more than one year prior to the filing date of this application.

SUMMARY

The following are the most outstanding and distinguishing characteristics of this new variety when grown under normal horticultural practices in Stuttgart, Germany.

1. Single flowers with a blue-violet flower color;
2. Rich flowering; and
3. Medium growth.

DESCRIPTION OF THE PHOTOGRAPH

This new *Dianthus* plant is illustrated by the accompanying photograph which shows overall habit of the plant. The photograph is of a plant approximately five-months-old grown in Stuttgart, Germany in April 2011. The colors shown are as true as can be reasonably obtained by conventional photographic procedures.

DESCRIPTION OF THE NEW VARIETY

The following detailed descriptions set forth the distinctive characteristics of 'KLEDG13146'. The data which define these characteristics were collected from asexual reproductions carried out in Stuttgart, Germany. Data was collected on five-month-old plants grown indoors in Stuttgart, Germany in May 2013. Color references are to The R.H.S. Colour Chart of The Royal Horticultural Society of London (R.H.S.), 5$^{th}$ edition (2007).

Classification:
*Family.*—Caryophyllaceae.
*Species.*—*Dianthus* sp.
*Common name.*—Garden carnation.

Parentage:
*Female.*—Proprietary *Dianthus* line 'DCP 06 060'.
*Male.*—*Dianthus* line 'N6'.

Propagation:
*Type.*—Vegetative.
*Time to produce a rooted young plant.*—16 to 20 days.
*Root description.*—Fine, white.
*Rooting habit.*—Small, very good branched.

Plant description:

*Plant type*.—Spray.

*Plant form*.—Upright, round, bushy.

*Plant height*.—12.0 cm to 20.0 cm.

*Plant diameter or spread*.—15.0 cm.

Lateral branches:

*Length*.—8.0 cm to 12.0 cm.

*Diameter*.—0.5 cm to 1.5 cm.

*Internode length*.—0.8 cm to 1.0 cm.

*Node length*.—0.4 cm.

*Node diameter*.—0.4 cm.

*Texture*.—Smooth.

*Color*.—RHS 133B.

Foliage description:

*Arrangement*.—Opposite.

*Length*.—5.0 cm to 7.0 cm.

*Width*.—0.5 cm to 0.7 cm.

*Shape*.—Lanceolate.

*Apex*.—Acute.

*Base*.—Obtuse.

*Margin*.—Entire.

*Texture*.—Upper surface: Smooth. Lower surface: Smooth.

*Venation pattern*.—Parallel.

*Color*.—Immature leaves: Upper surface: RHS 133C. Lower surface: RHS 133D. Mature leaves: Upper surfaces: RHS 133B. Lower surface: RHS 133C. Venation: RHS 133C.

Flower description:

*Flower type and habit*.—Single, radial.

*Fragrance*.—Present, strong.

*Natural flowering season*.—May to October.

*Flower longevity*.—10 to 16 days (medium to high).

Flower buds:

*Length*.—1.5 cm.

*Diameter*.—0.5 cm.

*Shape*.—Tall cylinder.

*Color*.—RHS 133C at the base of the bud and RHS 184A at the apex of the bud.

Corolla:

*Quantity of petals/arrangement*.—5.

*Corolla height*.—0.5 cm.

*Petal length*.—1.5 cm.

*Petal width*.—1.5 cm.

*Petal shape*.—Round.

*Petal apex*.—Round.

*Petal base*.—Obtuse.

*Petal margin*.—Crenate.

*Petal texture*.—Upper surface: Smooth. Lower surface: Smooth.

*Petal color*.—Immature: Upper surface: RHS 78A. Lower surface: RHS 80C. Mature: Upper surface: RHS 84B and RHS 72A. Lower surface: RHS 84B and RHS 84C. Calyx: Quantity of sepals: 5. Calyx height: 1.5 cm. Calyx diameter, at the apex: 0.5 cm. Sepal texture: Upper surface: Smooth. Lower surface: Smooth. Sepal color: Upper surface: RHS 133C. Lower surface: RHS 137C.

Peduncles:

*Length*.—10.0 cm to 12.0 cm.

*Diameter*.—0.2 cm.

*Strength*.—Moderate.

*Texture*.—Smooth.

*Color*.—RHS 133B.

Reproductive organs:

*Stamens*.—Quantity: Numerous. Filament length: 1.5 cm. Filament color: RHS 56D. Anther length: 0.1 cm to 0.2 cm. Anther diameter: Less than 0.1 cm. Anther color: RHS 95D. Pollen amount: Moderate.

*Pistils*.—Quantity: 1. Pistil length: 0.5 cm. Style length: 1.5 cm. Style color: RHS 95D. Stigma shape: Filamentous. Stigma color: RHS 71A. Ovary size: 0.5 cm. Ovary shape: Ovate. Ovary color: RHS 137D.

Fruits/seeds: Absent.

Disease/insect resistance: Normal resistance, no special resistance against diseases and insects.

COMPARISON WITH PARENTAL LINES AND KNOWN VARIETY

'KLEDG13146' is distinguished from its parental lines as described in Table 1:

TABLE 1

Comparison with Parental Lines

| Trait | Variety 'KLEDG13146' | Female parent 'DCP 06 060' | Male Parent 'N6' |
|---|---|---|---|
| Flowering | Rich flowering | Medium | Low |
| Flower fullness | Single | Double | Single |

KLEDG13146' is most similar to the commercial *Dianthus* plant named 'Velvet' (U.S. Plant Pat. No. 9,758). Differences between the two varieties are described in Table 2:

TABLE 2

Comparison with Similar Variety

| Trait | Variety 'KLEDG13146' | Commercial line 'Velvet' |
|---|---|---|
| Flower color | Blue - violet | Dark red |
| Growth | Medium | Compact |

We claim:

1. A new and distinct variety of *Dianthus* plant named 'KLEDG13146' as illustrated and described herein.

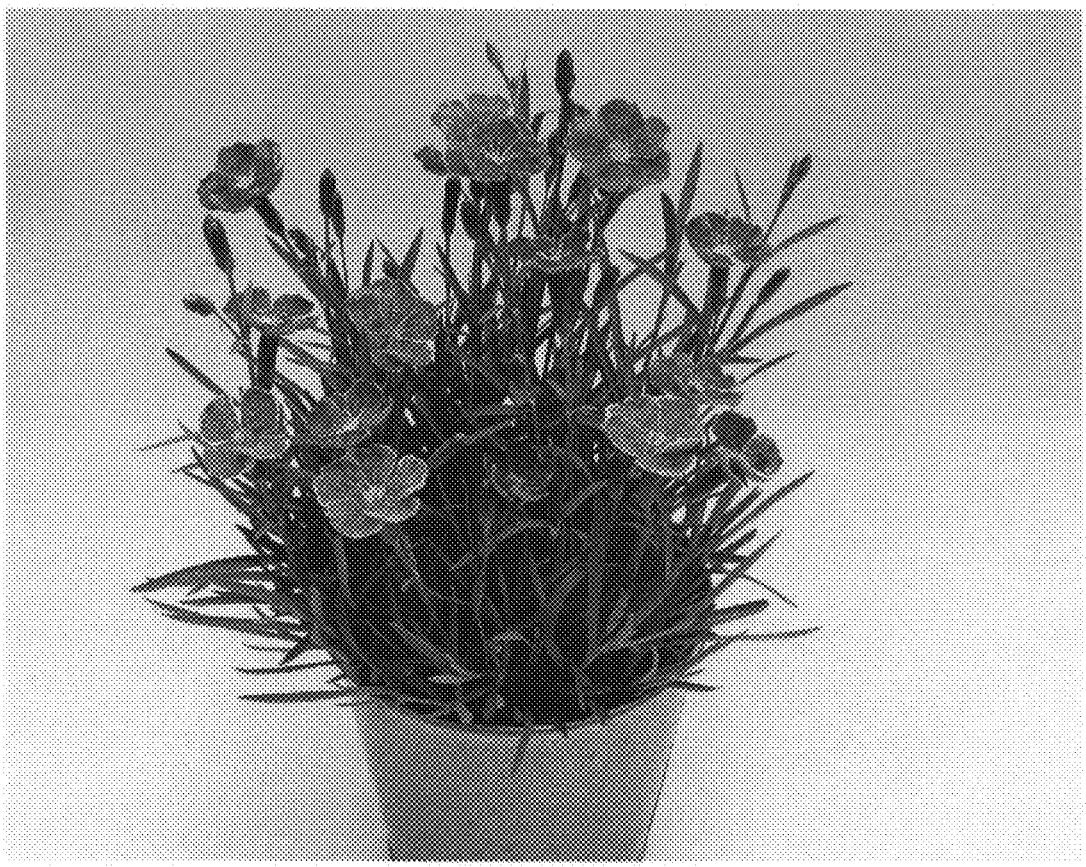

* * * * *